(12) United States Patent
Rust

(10) Patent No.: US 11,141,508 B2
(45) Date of Patent: Oct. 12, 2021

(54) MACRO-ENCAPSULATED THERAPEUTIC CELLS, DEVICES, AND METHODS OF USING THE SAME

(71) Applicant: Seraxis, Inc., Germantown, MD (US)

(72) Inventor: William L Rust, Germantown, MD (US)

(73) Assignee: Seraxis, Inc., Germantown, MD (US)

( * ) Notice: Subject to any disclaimer, the term of this patent is extended or adjusted under 35 U.S.C. 154(b) by 121 days.

(21) Appl. No.: 16/289,626

(22) Filed: Feb. 28, 2019

(65) Prior Publication Data

US 2019/0269832 A1 Sep. 5, 2019

Related U.S. Application Data

(60) Provisional application No. 62/637,085, filed on Mar. 1, 2018.

(51) Int. Cl.

| | |
|---|---|
| *A61K 35/39* | (2015.01) |
| *A61L 31/08* | (2006.01) |
| *A61P 3/10* | (2006.01) |
| *A61L 31/04* | (2006.01) |
| *A61P 5/48* | (2006.01) |
| *A61P 5/50* | (2006.01) |
| *A61L 27/38* | (2006.01) |
| *A61L 27/54* | (2006.01) |
| *A61K 9/50* | (2006.01) |
| *A61K 35/00* | (2006.01) |

(52) U.S. Cl.
CPC ............ *A61L 31/08* (2013.01); *A61K 9/5036* (2013.01); *A61K 35/39* (2013.01); *A61L 27/3804* (2013.01); *A61L 27/54* (2013.01); *A61L 31/04* (2013.01); *A61P 3/10* (2018.01); *A61P 5/48* (2018.01); *A61P 5/50* (2018.01); *A61K 2035/11* (2013.01)

(58) Field of Classification Search
None
See application file for complete search history.

(56) References Cited

U.S. PATENT DOCUMENTS

| | | | |
|---|---|---|---|
| 4,743,545 A | 5/1988 | Torobin | |
| 5,545,423 A * | 8/1996 | Soon-Shiong | A61K 9/0024 424/484 |
| 2005/0180957 A1 | 8/2005 | Scharp et al. | |
| 2008/0292690 A1 | 11/2008 | Wang | |
| 2009/0011033 A1 * | 1/2009 | Hauser | A61P 43/00 424/494 |

(Continued)

FOREIGN PATENT DOCUMENTS

| | | |
|---|---|---|
| WO | WO 93/21266 A1 | 10/1993 |
| WO | WO 94/10950 A1 | 5/1994 |

(Continued)

OTHER PUBLICATIONS

Storrs et al. (Ann NY Acad Sci. 2001;944:252-266) (Year: 2001).*

(Continued)

*Primary Examiner* — Ernst V Arnold
(74) *Attorney, Agent, or Firm* — Foley & Lardner LLP

(57) ABSTRACT

Described are macro-capsules, barriers, and devices that can be used to prepare therapeutic cell implants, methods of encapsulating therapeutic cells, and methods of using the encapsulated cells in the treatment of disease.

34 Claims, 11 Drawing Sheets

(56) References Cited

U.S. PATENT DOCUMENTS

| | | |
|---|---|---|
| 2014/0271843 A1 | 9/2014 | Ma et al. |
| 2016/0151541 A1 | 6/2016 | Hasilo et al. |
| 2016/0199311 A1 | 7/2016 | Wang |
| 2017/0258852 A1 | 9/2017 | Ma et al. |

FOREIGN PATENT DOCUMENTS

| | | |
|---|---|---|
| WO | WO 2010/032242 A1 | 3/2010 |
| WO | WO 2016/187225 A1 | 11/2016 |

OTHER PUBLICATIONS

Agulnick, A.D. et al., Insulin-producing endocrine cells differentiated in vitro from human embryonic stem cells function in macroencapsulation devices in vivo, Stem Cells Translational Medicine, 2015: 4:1214-1222.

An, D., Designing a retrievable and scalable cell encapsulation device for potential treatment of type I diabetes, Proc. Natl. Acad. Sci USA, Jan. 9, 2018; 115(2): E262-E272; (published online Dec. 26, 2017).

Basta, G. et al., Long-term metabolic and immunological follow-up of nonimmunosuppressed patients with type I diabetes treated with microencapsulated islet allografts, Diabetes Care, vol. 34, pp. 2406-2409, Nov. 2011.

Brunei, A. et al., Islet cell transplantation for the treatment of type I diabetes: recent advances and future challenges, Diabetes, Metabolic Syndrome and Obesity: Targets and Therapy 2014:7 211-223.

Chen, X. et al., Allotransplantation of sulphate glucomannan-alginate barium (SGA)-microencapsultated rat islets for the treatment of diabetes mellitus, Immunol. Invest., 38(7): 561-571 (2009).

Chen, X. et al., Novel sulfated glucomannan-barium-alginate microcapsules in islet transplantation: significantly decreased the secretion of monocyte chemotactic protein 1 and improved the activity of islet in rats, Transplantation Proc., 41, 4307-4312 (2009).

Lohr, J. M. et al., Encapsulated cells expressing a chemotherapeutic activating enzyme allow the targeting of subtoxic chemotherapy and are safe and efficacious: data from two clinical trials in pancreatic cancer, Pharmaceutics 2014, 6, 447-466.

Reddy, N.B. et al., Ability of modified glucomannan to sequestrate T-2 toxin in the gastrointestinal tract of chicken, Asian-Australas J. Anim. Sci., 17(2): 259-62 (2004).

Stiegler, P.B. et al., Cryopreservation of insulin-producing cells microencapsulated in sodium cellulose sulfate, Transplant Proc., 38(9): 3026-30 (2006).

Tuch, B.E. et al., Safety and viability of microencapsulated human islets transplanted into diabetic humans, Diabetes Care, 32(10):1887-9 (2009).

Vegas, A.J. et al., Long term glycemic control using polymer encapsulated, human stem-sell derived β-cells in immune competent mice, Nat. Med. 22(3): 306-311 (2016).

Vegas, A.J. et al., Combinatorial hydrogel library enables identification of materials that mitigate the foreign body response in primates, Nat. Biotechnol. 34(3): 345-352 (2016).

Wang, T. et al., Successful allotransplantation of encapsulated islets in pancreatectomized canines for diabetic management without the use of immunosuppression, Transplantation, 85(3): 331-337 (2008).

Weber et al., CellMAC: a novel technology for encapsulation of mammalian cells in cellulose sulfate/pDADMAC capsules assembled on a transient alginate/$Ca^{2+}$ scaffold, Journal of Biotechnology, Nov. 9, 2004, 114(3):315-326.

Weir, G.C., Islet encapsulation: advances and obstacles, Diabetologia 56(7): 1458-1461 (2013).

International Search Report and Written Opinion regarding Int'l Appl. No. PCT/US2019/019880, dated May 23, 2019, 14 pps.

\* cited by examiner

Human antigen
Nucleus/cellulose sulfate

Human antigen
Nucleus/cellulose
sulfate

Fig. 3A  Macro-capsules formed without konjac glucomannan
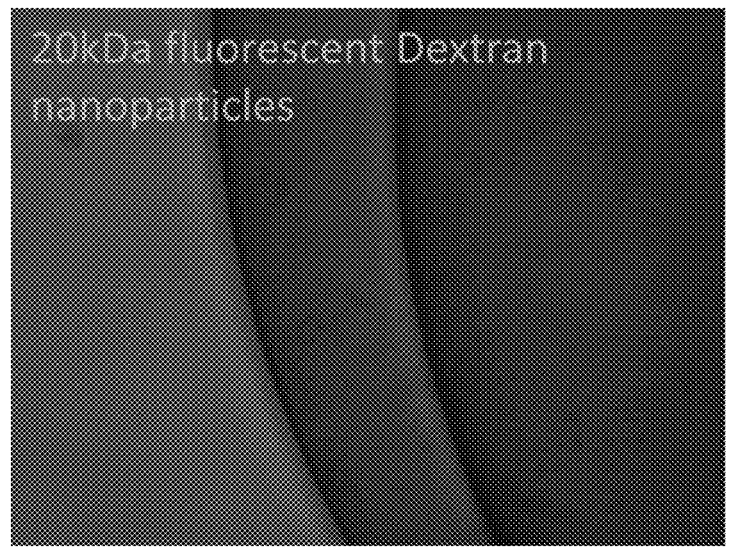
Fig. 3B  Macro-capsules formed with konjac glucomannan
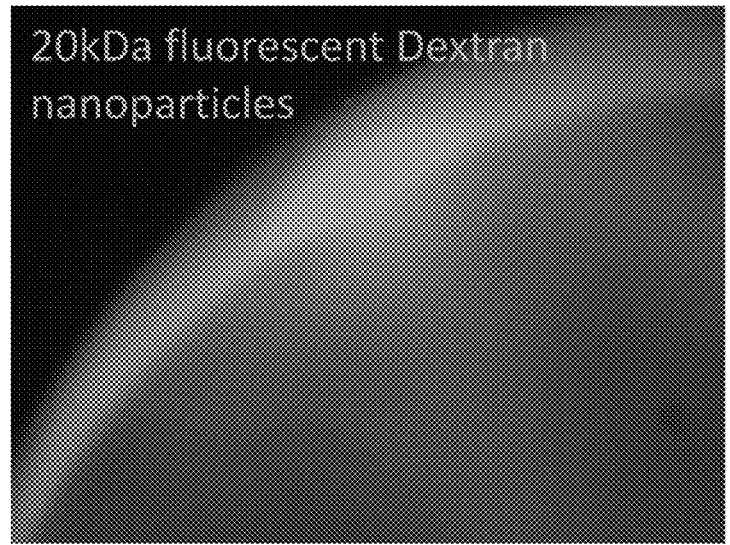

Before implant

Explant after 9 days

Explant after 47 days

*(x)* Macro-capsules
*(y)* Surgical mesh
*(z)* Tab (x) Macro-capsules
(y) Surgical mesh
(z) Tab

MACRO-ENCAPSULATED THERAPEUTIC CELLS, DEVICES, AND METHODS OF USING THE SAME

RELATED APPLICATION

This application claims priority under 35 U.S.C. § 119(e) to U.S. Provisional Application 62/637,085 filed Mar. 1, 2018, the entire contents of which are incorporated herein by reference.

FIELD

The present disclosure relates generally to the field of cell transplantation and encapsulation of therapeutic cells. Described are macro-capsules for encapsulating therapeutic cells, processes for encapsulating therapeutic cells, and related methods of use for treating diseases such as diabetes.

BACKGROUND

The following discussion is provided to aid the reader in understanding the disclosure and is not admitted to describe or constitute prior art thereto.

Diabetes and Insulin

Diabetes mellitus (i.e., diabetes) is a disease in which the body's ability to produce or respond to the hormone insulin is impaired, resulting in abnormal metabolism of carbohydrates and elevated levels of glucose in the blood and urine. The disease is subdivided into several sub-types, described alternatively as Type 1 diabetes mellitus, insulin-dependent diabetes mellitus (IDDM), mature onset diabetes of the young (MODY), latent adult diabetes (LADA), brittle diabetes, lean diabetes, Type 1.5, Type 2, Type 3, obesity-related diabetes, gestational diabetes, and other nomenclature accepted by the field.

In general, a subject with insulin-dependent diabetes is required to administer exogenous insulin to sufficiently lower blood glucose. A non insulin-dependent subject may sufficiently lower blood glucose with pharmaceutical intervention including classes of drugs that enhance sensitivity to insulin, or excretion of glucose. A subject with insulin-dependent diabetes may benefit from a cell replacement therapy in which insulin-producing cells are implanted to the subject whether that disease is labeled as type 1, MODY, LADA, brittle, lean, Type 1.5, Type 2, Type 3, obesity related diabetes or any combination thereof.

Type I diabetes is usually diagnosed in children and young adults, and was previously known as juvenile diabetes. Only 5-10% of people with diabetes have this form of the disease. Mature onset diabetes is the most common form of the disease, and it arises due to the impairment or destruction of insulin-producing beta cells, development of insulin resistance, or both impairment of insulin-producing beta cells and development of insulin resistance. Diabetes can arise in non-obese adults and children due to a combination of genetic and environmental factors. In obese adults and children, the pancreas may attempt to make extra insulin in order to control blood glucose, but over time it is unable to keep up and maintain blood glucose at normal levels. The body may also become less sensitive to the insulin that is produced. Prolonged over-activity of the insulin secreting beta cells may lead to beta-cell dysfunction and death.

Diabetes symptoms vary depending on how much a subject's blood glucose fluctuates. Some people, especially those with prediabetes or non-insulin dependent diabetes, may not experience symptoms initially. In Type I diabetes, symptoms tend to come on quickly and are more severe.

Some of the signs and symptoms of Type I and Type II diabetes include, but are not limited to, increased thirst; frequent urination; extreme hunger; unexplained weight loss; presence of ketones in the urine (ketones are a byproduct of the breakdown of muscle and fat that happens when there is not enough available insulin); fatigue; irritability; blurred vision; slow-healing sores; frequent infections, such as gums or skin infections and vaginal infections.

Encapsulated Cells

It has long been a goal of biomedical research to create a system for encapsulating cells within a semi-permeable barrier that would enable foreign cells to survive within an immune-competent human host (Weir, *Diabetologia*, 56(7): 1458-61 (2013)). To achieve this goal, the encapsulating barrier must allow passage of gases, nutrients, and waste, but the barrier must also be impermeable to immunocytes and their effector molecules that would target the cells for immune destruction. The barrier must also avoid stimulating inflammation, fibrosis or other host defenses against foreign materials.

The most predominant barrier materials reported in the published scientific literature are the carbohydrate polymers sodium alginate and cellulose sulfate (see, e.g., Tuch et al., *Diabetes Care*, 32(10):1887-9 (2009); Basta et al., *Diabetes Care*, 34(11):2406-9 (2011); Löhr et al., *Pharmaceutics*, 6(3):447-66 (2014)).

Sodium alginate forms a gel-like matrix in the presence of divalent cations, such as calcium or barium. Sodium alginate matrices are frequently supplemented by a layer of poly-L-lysine or poly-L-ornithine to decrease porosity.

Cellulose sulfate can be complexed with the copolymer poly(diallyldimethylammonium chloride) (pDADMAC) to form a membrane. Sodium alginate and cellulose sulfate have also been used in combination to form a barrier intermixed with alginate and sodium sulfate (Wang et al., *Transplantation*, 85(3):331-7 (2008); Weber et al., *J. Biotechnol.* 114(3):315-26 (2004)).

Cell Survival

There are few reports of these barriers enabling the survival and function of foreign cells within the body of immune-competent hosts for extended periods of time (i.e., at least six months; see Tuch, Basta, Löhr, Ma (*Designing a retrievable and scalable cell encapsulation device for potential treatment of type 1 diabetes*, PNAS|Published online Dec. 26, 2017). The general failure of encapsulated cells to function beyond a limited time is at least partially attributable to poor oxygen diffusion across the barrier leading to death or impairment of cell function or accumulation of fibrotic tissue around the barrier. To address this issue, one group has produced a form of alginate that is modified by a covalently linked chemical group comprising a triazol analog that they claim decreases the attachment of host macrophages to the alginate (see Vegas et al., *Nat. Biotechnol.*, 34(3):345-52 (2016)). This group produced micro-capsules of the modified alginate that were capable of enabling human, insulin secreting cells derived from embryonic stem cells to lower blood glucose in diabetic mice up to six months after implant to the peritoneal cavity (see Vegas et al., *Nat. Med.*, 22(3):306-11 (2016).

Retrieveability

A major drawback of microcapsules is that they cannot be completely retrieved from the host if the transplanted device becomes a safety risk to the patient or if the device ceases to function and needs to be replaced. It is generally accepted by the field that devices intended for human therapeutic use should be retrievable to be considered safe and practical for therapy.

Practical Therapeutic Dose

A separate group described a device comprised of alginate adhered to the surface of a woven nylon thread to create a long tubular structure (See Ma (Designing a retrievable and scalable cell encapsulation device for potential treatment of type 1 diabetes. PNAS|Published online Dec. 26, 2017). This shape is reported to be retrievable after implant to the peritoneal cavity unless portions of the alginate detach from the woven thread. Another group reported a planar macro-encapsulation device for subcutaneous implant that is retrievable (see D'AMOUR 2015, STEM CELLS TRANSLATIONALMEDICINE 2015; 4:1-9). These devices, however, are compromised by having a limited volume to contain therapeutic cells. It would be impractical to deliver a therapeutic dose to a human patient using the described devices. For example, a therapeutic dose of cells to treat an insulin-dependent diabetic weighing 60 kg is 600 million cells (Bruni 2015 Bruni A, et al. Diabetes Metab Syndr Obes. 2014 Jun. 23; 7:211-23). The described tubular device would need to be 60 meters long to contain that therapeutic dose. A 60 kg diabetic would need 40 of the described planar macroencapsulation devices to receive a therapeutic dose.

Insulin Release Kinetics

The pancreas is a highly vascularized organ that achieves fast systemic distribution of insulin and other pancreatic hormones. Each islet within the pancreas is proximal to a blood microvessel. The pancreatic circulation is also connected to the liver, a main site of action of pancreatic hormones. A healthy pancreas is therefore able to restore normal blood glucose levels within minutes of glucose fluctuation. Devices that are implanted to the peritoneal cavity lack proximity to the host vasculature leading to slow release of insulin to the circulation and long periods of hyperglycemia (Ma (Designing a retrievable and scalable cell encapsulation device for potential treatment of type 1 diabetes. PNAS|Published online Dec. 26, 2017). Human skin is poorly vascularized and also lacks proximity to the liver. As a result, subcutaneous implants are not expected to allow rapid systemic circulation of pancreatic hormones, leading to periods of hyperglycemia. Periodic hyperglycemia is a main contributor to morbidity of diabetes.

Thus, there remains a need in the art for encapsulation barriers that are capable of supporting the long-term survival of transplanted cells, that are retrievable and that can provide rapid distribution of secreted hormones, both in general, and specifically for the treatment of diabetes. The present disclosure fulfills those needs.

SUMMARY

Described herein are macro-encapsulation barriers and devices that can be used to prepare therapeutic cell transplants, methods of encapsulating therapeutic cells, and methods of using the encapsulated cells in the treatment of disease. The macro-encapsulated cells and devices are retrievable from the host, capable of containing a therapeutic dose of cells in a practical volume, and enable rapid distribution of secreted hormones.

In one aspect, the present disclosure provides a device comprising at least two macro-capsules encapsulating a plurality of therapeutic cells, the macro-capsule comprising a cylindrical shape and a diameter of at least 1.5 mm. In some embodiments, the macro-capsules comprise at least one barrier, the barrier comprising: (a) cellulose sulfate and glucomannan or glucomannan sulfate; or (b) sodium alginate. In some embodiments, the macro-capsules are attached to a substrate, such as a surgical mesh, in order to connect multiple macro-capsules into a single device capable of treating diabetes.

In some embodiments, the macro-capsule is attached to a piece of surgical mesh. The surgical mesh functions as a suture point to attach the device to the omentum or another site on the host. In some embodiments, a plurality of macro-capsules are attached to the same piece of surgical mesh. In some embodiments, the surgical mesh is nylon.

In some embodiments, the surgical mesh is round. In some embodiments, the surgical mesh is oblong. In some embodiments the surgical mesh contains a tab useful as a suture point for attaching the device to the omentum or another suitable site within the host.

In some embodiments, the macro-capsules are arranged radially around the mesh. In some embodiments, the macro-capsules are arranged in apposition along the mesh. In some embodiments, the macro-capsules are arranged to extend on opposite sides of the mesh.

In another aspect, the present disclosure provides a composition comprising a macro-capsule encompassing a plurality of therapeutic cells, the macro-capsule comprising at least one barrier, the barrier comprising: (a) cellulose sulfate and glucomannan or glucomannan sulfate; or (b) sodium alginate; wherein the macro-capsule is attached to a piece of surgical mesh to which at least one other macro-capsule is also attached.

In some embodiments, the composition further comprises a second barrier. In some embodiments, the second barrier comprises cellulose sulfate and glucomannan or glucomannan sulfate. In some embodiments, the second barrier does not comprise glucomannan or glucomannan sulfate.

In another aspect, the present disclosure provides a composition comprising a macro-capsule encompassing a plurality of therapeutic cells, the macro-capsule comprising at least a first barrier and a second barrier, wherein the first barrier is encompassed within the second barrier, wherein the macro-capsule has a diameter of at least 1.5 mm, wherein the macro-capsule is attached to a piece of surgical mesh to which at least one other macro-capsule is also attached.

In some embodiments, the therapeutic cells are insulin-producing cells.

In some embodiments, the second barrier comprises cellulose sulfate and glucomannan or glucomannan sulfate. In some embodiments, both the first and second barrier comprise cellulose sulfate and glucomannan sulfate. In some embodiments, the second barrier does not comprise glucomannan or glucomannan sulfate. In some embodiments, the first barrier comprises sodium alginate.

In another aspect, the present disclosure provides a composition comprising a macro-capsule encompassing a plurality of therapeutic cells, the macro-capsule comprising a cylindrical shape and a diameter of at least 1.5 mm, wherein the macro-capsule is attached to a piece of surgical mesh to which at least one other macro-capsule is also attached.

In some embodiments, the macro-capsule comprises at least a first barrier and a second barrier, wherein the first barrier is encompassed within the second barrier.

In some embodiments, the first barrier comprises: (a) cellulose sulfate and glucomannan or glucomannan sulfate; or (b) sodium alginate.

In some embodiments, the second barrier comprises cellulose sulfate and glucomannan or glucomannan sulfate.

In some embodiments, the therapeutic cells are insulin-producing cells, such as islet cells.

In some embodiments, the first barrier may comprise cellulose sulfate and glucomannan or glucomannan sulfate, and in some embodiments, the first barrier may comprise sodium alginate. In some embodiments, the sodium alginate is polymerized with divalent cations barium ($BaCl_2$) or calcium ($CaCl_2$).

In some embodiments, the composition may further comprise a second barrier. For example, in some embodiments, the second barrier may comprise cellulose sulfate and glucomannan or glucomannan sulfate. In some embodiments, the second barrier does not comprise glucomannan or glucomannan sulfate. In some embodiments, both the first and second barrier comprise cellulose sulfate and glucomannan or glucomannan sulfate.

In some embodiments of the foregoing aspects, the diameter of the macro-capsule is at least about 1.5 mm, at least about 1.6 mm, at least about 1.7 mm, at least about 1.8 mm, at least about 1.9 mm, at least about 2.0 mm, at least about 2.1 mm, at least about 2.2 mm, at least about 2.3 mm, at least about 2.4 mm, or at least about 2.5 mm.

In some embodiments of the foregoing aspects, the cellulose sulfate was polymerized with poly(diallyldimethylammonium chloride) (pDADMAC). For example, in some embodiments, the macro-capsule was washed with polymethylene-co-guanidine (PMCG) after polymerization with pDADMAC.

In some embodiments of the foregoing aspects, the macro-capsules are cylindrical.

In some embodiments of the foregoing aspects, a plurality of cylindrical macro-capsules are joined at one end.

In another aspect, the present disclosure provides methods of treating diabetes in a subject in need thereof, comprising implanting into a subject with diabetes any of the foregoing devices or compositions.

In some embodiments of the disclosed methods, the subject is an adult, while in some embodiments, the subject is a child. In some embodiments of the disclosed methods, the subject has Type I diabetes, while in some embodiments, the subject has Type II diabetes.

In some embodiments of the disclosed methods, the composition is implanted into the greater omentum or the peritoneal cavity of the subject. For example, the composition may be anchored to the omentum or implanted in an omentum pouch.

In some embodiments of the foregoing aspects, each macro-capsule is at least about 10 cm in length, at least about 11 cm in length, or at least 12 cm in length, or at least 13 cm in length, or at least 14 cm in length, or at least 15 cm in length, or at least 16 cm in length, or at least 17 cm in length, or at least 18 cm in length, or at least 19 cm in length, or at least 20 cm in length.

In some embodiments of the foregoing aspects, the macro-capsule contains at least about 50,000 cells per cm, at least about 60,000 cells per cm, at least about 70,000 cells per cm, at least about 80,000 cells per cm, at least about 90,000 cells per cm, at least about 1000,000 cells per cm.

All of the macro-capsule compositions disclosed herein are suitable for preparing devices comprising two or more macro-capsules that are attached to a surgical mesh or other substrate in order to form a larger scale structure. For example, in some embodiments, the macro-capsules to be incorporated into such a device may comprises at least one barrier, the barrier comprising (a) cellulose sulfate and glucomannan or glucomannan sulfate; or (b) sodium alginate. In some embodiments, the macro-capsules may comprise at least a first barrier and a second barrier, wherein the first barrier is encompassed within the second barrier.

A composition or device according to any one of the foregoing aspects or embodiments, for use in treating diabetes in a subject in need thereof.

Use of a composition or device according to any one of the foregoing aspects or embodiments in the manufacture of a medicament for the treatment of diabetes.

The following detailed description is exemplary and explanatory, and is intended to provide further explanation of the invention.

BRIEF DESCRIPTION OF THE DRAWINGS

FIGS. 3A-3B show permeability of macrocapsules to 20 kDa dextran particles. Incorporation of konjac glucomannan or konjac glucomannan sulfate into a membrane of cellulose sulfate can increase the permeability of the membrane. Macro-capsules formed without konjac glucomannan sulfate do not allow the passage of 20 kDa fluorescent nanoparticles to the inside of the macro-capsules (A). The interior of the macro-capsules are not fluorescent after rinsing. Macro-capsules formed with konjac glucomannan sulfate do allow the passage of 20 kDa fluorescent nanoparticles to the inside of the macro-capsules (B). The interior of the macro-capsules are fluorescent after rinsing.

DETAILED DESCRIPTION

Figure 1A:
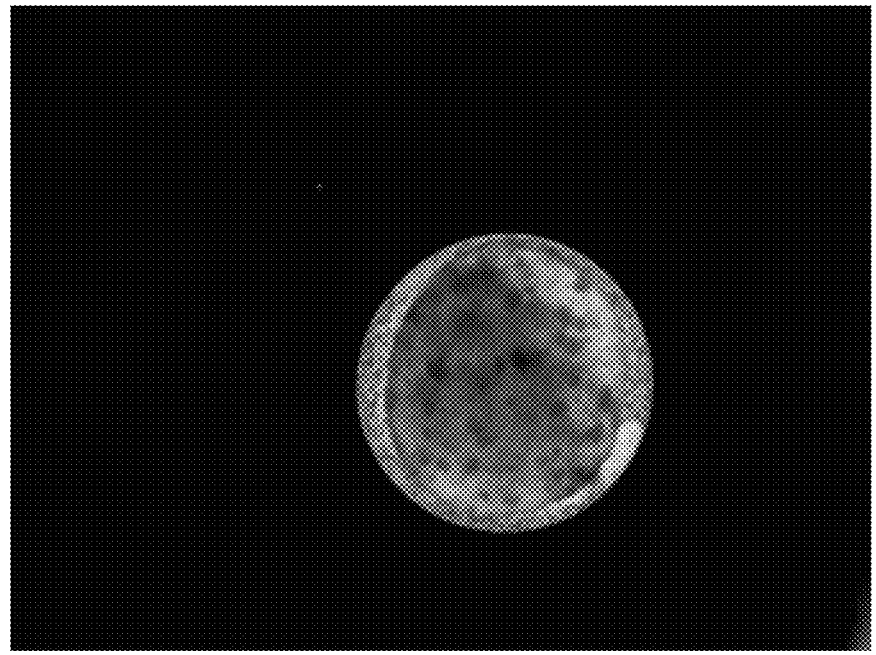
FIGS. 1A-1D show macro-capsules. (A) Brightfield image of spherical macro-capsule composed of cellulose sulfate and konjac glucomannan. Inner capsule contains multiple clusters of therapeutic cells. Original image 100× magnification. (B) Immunofluorescence of human antigen-stained macro-capsules removed from a normal rat 3 weeks after implant at 40× magnification. The surface of the macro-capsule has no adhered host cells nor evidence of inflammation or fibrosis. (C) Macro-capsules not formed with konjac glucomannan sulfate, but otherwise identical to macro-capsule shown in (B) at 24× magnification. The macro-capsules formed without konjac glucomannan sulfate have an overgrowth of host cells around the macro-capsule and no living human cells within the macro-capsules. (D) Brightfield image of cylindrical macro-capsule. Inner capsule is composed of alginate hydrogel and contains multiple clusters of therapeutic cells. Outer capsule closely adheres to inner capsule and is composed of cellulose sulfate and konjac glucomannan.
Figure 1B:
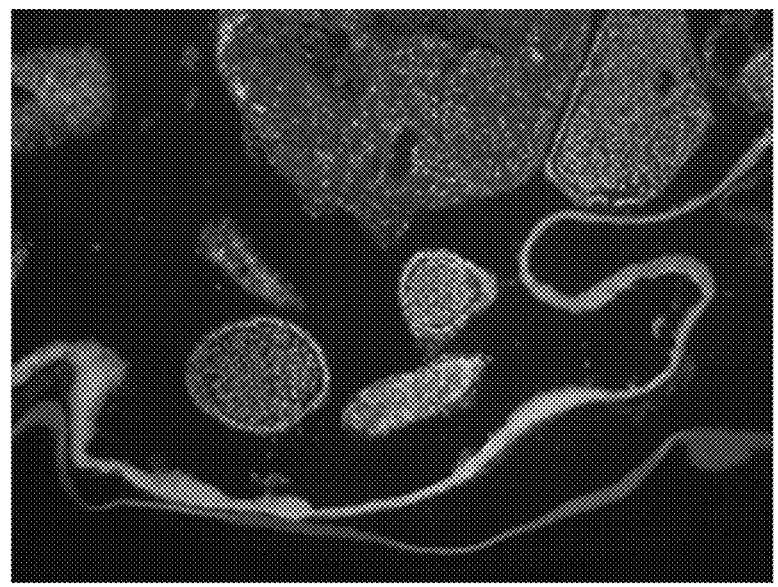
Figure 1C:
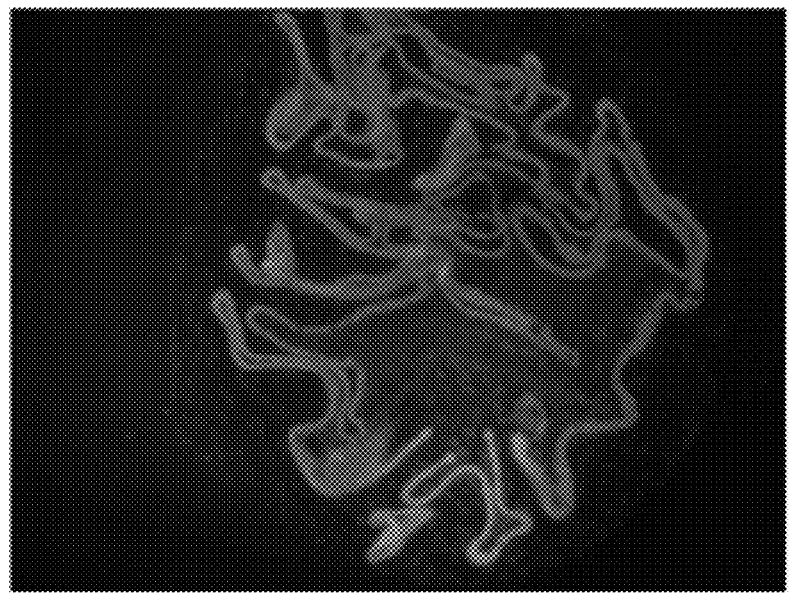
Figure 1D:
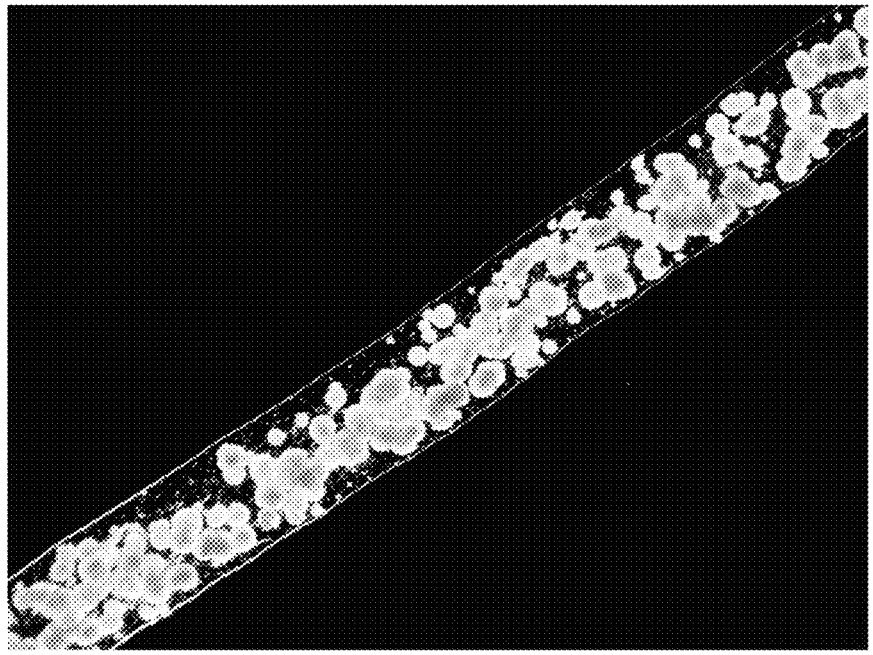

Described herein are macro-encapsulation compositions and devices that can be used in therapeutic cell transplants, methods of preparing encapsulated therapeutic cells, and related methods of use, such as in the treatment of disease in a subject in need thereof.

The survival of the encapsulated cells is impacted by the immune protection of the barrier membranes and by the diffusion characteristics of biological molecules across the membranes. The long-term efficacy of the implant is dependent upon the physical integrity of the device and on the biocompatibility of the device, or low stimulation of inflammation, fibroses, and other foreign body responses of the host, as well as oxygen diffusion, density of the encapsulated cells, and the location of engraftment within a host. The ability to practically deliver a therapeutic dose of cells is dependent upon the loading density of therapeutic cells. The ability to rapidly distribute secreted factors is dependent upon the location of engraftment within the host and the ability to form proximal connections to the host vasculature.

This disclosure describes novel macro-capsule compositions formed from cellulose sulfate that enable survival and function of encapsulated cells for longer than six months after implant of the cells into an immune competent host. This disclosure further describes novel macro-capsule shapes that facilitate capsule retrieval from a living host. The disclosed encapsulation barriers can comprise, in addition to cellulose sulfate, the carbohydrate polymers konjac glucomannan or konjac glucomannan sulfate, which help to control barrier porosity and limit fibrosis. The disclosure also provides a novel macro-capsule double-barrier membrane design with a diameter greater than 1.5 mm that permits the implant and engraftment of a high density of therapeutic cells. The disclosure also provides for the formation of non-spherical macro-capsules. The disclosure also provides for the attachment of a plurality of macrocapsules together to scale the size of the device for a larger therapeutic dose. Further, the process for preparing the disclosed macro-capsules may comprise a sequential polymerization step comprising polymethylene-co-guanidine (PMCG) to improve the mechanical properties of the membrane. The macro-capsules formed using the disclosed materials and techniques can be used to treat diabetes in fully immune-competent subjects by implanting the encapsulated cells into a subject, for example, by attachment to the greater omentum, or into a pouch surgically formed from the greater omentum or other implant sites that are commonly used for such cell-based treatments.

I. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used here, "macro-capsule" refers to a polymer-based composition for encapsulating therapeutic cells. The precise size and shape of the macro-capsule is not particularly limited and may be determined by the methods and materials used to make the macro-capsule. Further, the disclosed macro-capsules may comprise more than one layer (i.e., barrier or membrane) of polymers encapsulating the therapeutic cells.

As used herein, the terms "barrier" or "membrane" refer to a layer of a macro-capsule composed of at least one polymer. The terms "barrier" and "membrane" may be used interchangeably throughout this disclosure.

As used herein, the term "hydrogel" refers to a porous matrix created by aggregates of carbohydrate polymers, such as alginate, bound together by ionic bonding with divalent cations, such as calcium or barium.

As used herein, "long-term," when used in relation to the survival and functioning of foreign therapeutic cells used in a cell-based therapy/implant, means a period of at least six months or longer.

As used herein, the phrases "therapeutically effective amount" means an amount of encapsulated cells transplanted into a subject that provides the specific pharmacological effect for which the cells are transplanted, i.e. to produce insulin and regulate blood glucose. It is emphasized that a therapeutically effective amount of encapsulated cells will not always be effective in treating diabetes in a given subject, even though such concentration is deemed to be a therapeutically effective amount by those of skill in the art. For convenience only, exemplary amounts are provided below.

Those skilled in the art can adjust such amounts in accordance with standard practices as needed to treat a specific subject. The therapeutically effective amount may vary based on the site of implantation, the age and weight of the subject, and/or the subject's condition, including the severity of the subject's disease, the subject's diet, and/or the subject's overall health.

The terms "treatment" or "treating" as used herein with reference to diabetes refer to one or more of: reducing, ameliorating or eliminating one or more symptoms or co-morbidities of diabetes, such as hyper- and hypo-glycaemia, heart disease, renal disease, hepatic disease, retinopathy, neuropathy, non-healing ulcers, periodontal disease; reducing the subject's reliance on exogenous insulin to regulate blood glucose, regulating the subject's blood glucose without the use of exogenous insulin; reducing the subject's percentage of glycosylated hemoglobin, or HbA1C levels; and/or reducing the subject's reliance on other pharmaceutical interventions, such as insulin sensitizers, enhancers of glucose excretion, and other treatment modalities known in the art.

The terms "individual," "subject," and "patient" are used interchangeably herein, and refer to any individual mammal subject, e.g., bovine, canine, feline, equine, or human.

II. Novel Macro-capsules and Barriers

Disclosed herein are novel macro-capsules and barriers and devices for encapsulating therapeutic cells such as pancreatic islet cells or other insulin-producing cells. The disclosed barriers comprise novel combinations of materials that improve the structural integrity of the capsules relative to conventional encapsulation techniques, improve permeability relative to conventional encapsulation techniques to increase passive diffusion of molecules to the encapsulated cells, reduce the occurrence of fibrosis, facilitate the manufacture of the capsules, and the disclosed macro-capsules possess unique structural characteristics that increase the survival of the encapsulated cells, reduce the occurrence of fibrosis, facilitate recruitment of the host vasculature to the device, facilitate implant to and retrieval from the host, and enable scaling of the device to deliver a therapeutic dose to large mammals.

Conventional means of encapsulating cells (such as insulin-producing cells) generally comprised alginate capsules, cellulose sulfate capsules, or hydrogels, each of which is discussed briefly herein.

Conventional alginate capsules that have been used to encapsulate insulin-producing cells are formed through the polymerization of sodium alginate around the insulin-producing cells in the presence of a divalent cation such as calcium or barium. This forms a hydrogel in which the insulin-producing cells are fixed in place. Attempts to improve the performance of these hydrogel capsules include: modification of the alginate to reduce cellular attachment; coating the capsules with a synthetic polymer such as poly-L-lysine or poly-L-ornithine to reduce permeability; modulating the ratio of mannuronic or guluronic monomeric residues to improve biocompatibility, and: rinsing in sodium citrate to liquefy the center of the capsules.

Conventional cellulose sulfate capsules that have been used to encapsulate insulin-producing cells are formed through the polymerization of cellulose sulfate and poly (diallyldimethylammonium chloride) (pDADMAC). These capsules differ from alginate hydrogels in that they are comprised of a flexible membrane surrounding a hollow core. These capsules are more fragile than alginate hydrogels due to their facile compressibility. These capsules are challenging to manufacture because unreacted pDADMAC on the surface of freshly made capsules irreversibly polymerize with other capsules that they may contact.

Conventional alginate hydrogel and cellulose sulfate capsules are microcapsules with a diameter generally 600 micrometers or less. It is generally accepted that smaller capsules are preferred over larger capsules, as the surface to volume ratio is greater, allowing for faster diffusion of gases and molecules.

After these conventional micro-capsules are implanted within an animal host, host cells including macrophages and fibroblasts adhere to the surface of the capsules. These cells will, over a period of weeks, deposit extracellular matrix proteins that constitute a fibrotic plaque around the foreign capsule. These fibroses inhibit diffusion to and from the cells within the capsules leading to loss of function and cell death.

In contrast to conventional micro-capsules, the disclosed macro-capsules demonstrate dramatically reduced recruitment and adhesion of host macrophages and fibroblasts and hence reduced deposition of fibrotic plaques. This property is the result of the unique combination of: high biocompatibility of cellulose sulfate/pDADMAC, konjac glucomannan or konjac glucomannan sulfate, and macro-capsule size and shape. Cells within these capsules are therefore able to survive and function long-term, or at least six months.

In contrast to conventional micro-capsules, the disclosed macro-capsules can be attached to the greater omentum. Attachment to the greater omentum facilitates the recruitment of host vasculature from the omentum to the macro-capsules. Proximity to the omental vasculature enables rapid systemic distribution of secreted factors.

The disclosed macro-capsules can comprise at least one barrier formed by mixing a carbohydrate polymer with anti-inflammatory and anti-coagulant properties with cellulose sulfate prior to polymerization with pDADMAC. The presence of the anti-inflammatory anti-coagulant reduces the recruitment and adhesion of host cells and the formation of fibroses. This process also increases the permeability of the barrier membrane to permit diffusion of the membrane to essential biological molecules. Konjac glucomannan or Konjac glucomannan sulfate are non-limiting examples of such a carbohydrate polymer. Other examples are heparin sulfate and chondroitin sulfate.

Glucomannan (i.e. konjac glucomannan) is a neutral polysaccharide harvested from the root of the konjac plant (*Amorphophallus konjac*). Glucomannan sulfate can be formed by the chemical addition of a sulfate group to free hydroxyl groups of the glucose monomers. This process can be achieved, for example, by esterification in the presence of pyridine sulfate in a suitable solvent such as dimethyl formamide, dimethyl sulfoxide, or one of the class of ionic solvents. Glucomannan sulfate polymers have a similar viscosity to cellulose sulfate and at low concentration do not inhibit the formation of cellulose sulfate/pDADMAC macro-capsules. Modified forms of glucomannan are known in the art (see, e.g., Reddy et al., *Asian-Australas J. Anim. Sci.*, 17(2): 259-62 (2004); Chen et al., *Immunol Invest.*, 38(7):561-71 (2009)), thus, for the purposes of this disclosure, "glucomannan" can refer to modified or unmodified glucomannan.

Furthermore, glucomannan and glucomannan sulfate have anti-coagulant properties. As shown herein, incorporation of glucomannan into cell-encapsulating macro-capsules decreases the deposition of fibroses. This is the first demonstration of glucomannan reducing the formation of fibroses when intermixed with the cellulose sulfate membrane of a macro-capsule. Furthermore, glucomannan provides the additional benefit of increasing the porosity of cellulose sulfate/pDADMAC membranes, allowing for the passive diffusion of molecules of at least 20 kDa through the macro-capsule barrier.

Accordingly, in some embodiments, the disclosed macro-capsules comprise at least one barrier layer comprising cellulose sulfate and glucomannan. In some embodiments, the disclosed macro-capsules comprise at least two barrier layers comprising cellulose sulfate and glucomannan.

Further, it is recognized in the art that it is difficult to form macro-capsules around a high density of cells. At high density, cells and cell clusters cross the membrane, compromising the integrity of the barrier. A high density of cells is preferred to enable transplant of a therapeutic quantity of cells in a small volume. A high density of cells is more than 2 million cells per milliliter of encapsulating polymer solution.

For example, conventional cellulose sulfate capsules have a diameter equal to or less than 600 µm and are formed with a single membrane of cellulose sulfate polymerized by pDADMAC (see, e.g., Stiegler et al., *Transplant Proc.*, 38(9):3026-30 (2006)). As cell density increases, the probability that a cell will be lodged within the polymerized membrane during the polymerization step also increases. When this occurs, it creates a defect to the membrane that causes failure of the immune-protective barrier.

Conventional capsules are formed by dropping a mixture of cells and liquid cellulose sulfate or liquid alginate into a polymerizing bath. The cells are distributed evenly through the droplet. Higher density therefore increases the probability that a cell will be exposed on the surface of the capsule. The cylindrical shape described here are formed by expelling the mixture of cells and liquid alginate into the polymerizing bath through a submerged blunt-end syringe needle. The dynamics of a fluid flowing through a syringe needle dictates that the cells will be concentrated towards the center of the cylinder being formed. Therefore, a high density of cells can be encapsulated within this shape with a low probability that the cells will be exposed at the surface of the capsule. The second barrier formed around these fixed cells virtually eliminates the possibility of a cells being exposed at the surface of the capsule.

The disclosed macro-capsules comprise a double barrier structure and have a diameter of at least about 1.5 mm. This design ensures the mechanical integrity of the macro-capsules and contributes to increasing the long-term stability of the macro-capsules in vivo. Moreover, the size of the macro-capsule permits the encapsulation of a high density of therapeutic cells.

A high density of therapeutic cells may be encapsulated within a macro-capsule with a diameter of 1.5 mm or greater. In some embodiments, the disclosed macro-capsules can be composed of a first barrier comprising alginate. In some embodiments, the disclosed macro-capsules can be composed of a first barrier comprising cellulose sulfate polymerized with pDADMAC. The first barrier can be rinsed with polymethylene-co-guanidine (PMCG). Subsequently, a second barrier comprising cellulose sulfate and, optionally, glucomannan or glucomannan sulfate, can be formed around the first barrier and, optionally, subsequently rinsed with PMCG, thus forming a double-barrier macro-capsule. The first barrier directly encompasses the therapeutic cells such that the second barrier can be formed without interference from cells and/or cell debris. Moreover, the second barrier is the only barrier that directly contacts the host after the macro-capsules are implanted.

In some embodiments, the disclosed macro-capsules comprise at least 1, at least 2, or at least 3 barriers. The barriers making up the macro-capsule may comprise the same or different materials. For examples, the barriers may be formed from cellulose sulfate; cellulose sulfate and glucomannan; cellulose sulfate and glucomannan sulfate; sodium alginate; cellulose sulfate and sodium alginate; sodium alginate and glucomannan sulfate; and/or cellulose sulfate, sodium alginate, and glucomannan sulfate. In some embodiments, only the outer barrier comprises glucomannan or glucomannan sulfate because only this layer of the macro-capsule will directly interact with the host after implantation. Other polymers that can be used in place of glucomannan or glucomannan sulfate are heparin sulfate and chondroitin sulfate.

In some embodiments, the disclosed macro-capsules are at least 1.5 mm in diameter. For example, the disclosed macro-capsules may have a diameter of about 1.5 mm, about 1.6 mm, about 1.7 mm, about 1.8 mm, about 1.9 mm, about 2.0 mm, about 2.1 mm, about 2.2 mm, about 2.3 mm, or about 2.4 mm. Diameters of 1.5 mm and larger result in decreased formation of fibroses after transplant to the host.

In some embodiments, the disclosed macro-capsules are at least 10 cm in length. For example, the disclosed macro-capsules may have a length of at least about 10 cm, at least about 11 cm, at least about 12 cm, at least about 13 cm, at least about 14 cm, at least about 15 cm, at least about 16 cm, at least about 17 cm, at least about 18 cm, at least about 19 cm, at least about 20 cm, or more. Having a macro-capsule of sufficient length makes the macro-capsule easier to retrieve from a subject in the event that the macro-capsule needs to be removed (i.e., increases retrievability).

The size and structure of the disclosed macrocapsules also allows the macro-capsules to encompass a therapeutically useful number of cells. For example, the disclosed macro-capsules may contain at least about 50,000 cells per cm, at least about 60,000 cells per cm, at least about 70,000 cells per cm, at least about 80,000 cells per cm, at least about 90,000 cells per cm, or at least about 1000,000 cells per cm or more.

In some instances in which more cells are needed, the disclosed macro-capsules may be joined end-to-end or weaved together.

In some embodiments, the disclosed macro-capsules are not spherical. A preferred shape is a cylindrical tube. The cylindrical tube has a diameter of at least 1 mm and is not limited in length. A cylindrical tube has a high surface to volume ratio to enable adequate diffusion while facilitating the retrieval of the capsules from a living host. A small number of tubes are easier to remove than a large number of spherical macro-capsules. A second barrier membrane comprised of cellulose sulfate or cellulose sulfate and glucomannan or glucomannan sulfate enhances the physical integrity of the cylindrical tube, thus improving retrievability.

Spherical capsules are formed by dropping a mixture of cells and liquid cellulose sulfate or liquid alginate into a polymerizing bath. The cells are distributed evenly through the droplet. Higher density therefore increases the probability that a cell will be exposed on the surface of the capsule. The cylindrical shape described here is formed by expelling the mixture of cells and liquid alginate into the polymerizing bath through a submerged blunt-end syringe needle. The dynamics of a fluid flowing through a syringe needle dictates that the cells will be concentrated towards the center of the cylinder being formed. Therefore, a high density of cells can be encapsulated within this shape with a low probability that the cells will be exposed at the surface of the capsule. The second barrier formed around these fixed cells virtually eliminates the possibility of a cells being exposed at the surface of the capsule.

In some embodiments, the cylindrical macro-capsule is attached to a substrate. The substrate permits the device to be attached to the greater omentum of the host. Attachment to the greater omentum facilitates recruitment of the vasculature of the greater omentum to the device. Attachment to the greater omentum facilitates retrieval of the device. In some embodiments, the substrate is a piece of surgical mesh.

In some embodiments, a plurality of the disclosed tubular macrocapsules are joined to a common substrate. The structure of two or more joined tubular macrocapsules enables the device to be scaled to accommodate a therapeutic dose of any size. In some embodiments the substrate is a piece of surgical mesh.

In some embodiments the substrate has the shape of a rectangular strip to enable the attachment of a plurality of tubular macro-capsules in apposition or on opposite sides of the strip. In some embodiments, the substrate is circular to enable the attachment of a plurality of tubular macro-capsules radiating out from a central point of attachment. In some embodiments, the shape of the substrate has a tab that is useful for passing a suture to attach the substrate to the tissue of the host. In some embodiments the substrate has two or more tabs to attached the substrate to the tissue of the host.

III. Processes for Preparing the Disclosed Macro-capsules

Disclosed herein are processes for more efficiently forming macro-capsules for encapsulating therapeutic cells, such as insulin producing cells.

A quantity of therapeutic cells are suspended in a solution of cellulose sulfate to a density of 2 million cells per milliliter. The cellulose sulfate/cell mixture is dripped into a buffered solution containing the polymerizing agent pDADMAC. The size of the droplet, and hence the macro-capsule, can be carefully controlled using a droplet generator. This capsule represents the inner capsule. This process may produce spherical capsules.

In some embodiments, the therapeutic cells are suspended in a solution of sodium alginate to a density of 2 million cells per ml and dropped into a buffered polymerization bath containing a divalent cation such as calcium or barium. This process may produce spherical hydrogels.

In some embodiments, the therapeutic cells are suspended in a solution of sodium alginate to a density of 2 million cells per ml and loaded into syringe with a blunt-ended needle or medical grade tubing with an inner bore diameter of 1.5 mm. The tip of the needle or tube is submerged in a buffered polymerization bath containing a divalent cation such as calcium or barium. The alginate/therapeutic cell mixture is injected into the polymerization bath to produce a hydrogel in the form of a cylindrical tube. The rate of injection can be carefully controlled using a syringe pump.

The spherical inner capsule comprised of cellulose sulfate, the spherical inner capsule comprised of sodium alginate, or the cylindrical tube comprised of sodium alginate is soaked in a solution of pDADMAC and briefly rinsed in distilled water. The inner capsule is then dipped in a solution of cellulose sulfate and glucomannan to form the outer capsule.

Alternatively, the spherical inner capsule comprised of cellulose sulfate, the spherical inner hydrogel comprised of sodium alginate, or the cylindrical tube comprised of sodium alginate is soaked in a solution of cellulose sulfate and glucomannan. The inner capsule or tube is dropped into a solution of pDADMAC to form the outer capsule.

Macro-capsules comprising cellulose-sulfate polymerized with pDADMAC have a known tendency to strongly adhere to one another if allowed to come into contact after rinsing away the polymerization buffer containing pDADMAC. This results in aggregates of macro-capsules or macro-capsules that are physically damaged when separated.

As disclosed herein, this aggregation can be minimized or eliminated by adding in a sequential wash step with polymethylene-co-guanidine (PMCG) after polymerization of each macro-capsule barrier. For example, after polymerization of cellulose sulfate with pDADMAC, a sequential wash with PMCG eliminates adhesion between macro-capsules, thus producing individual macro-capsules that are physically intact. PMCG polymerization additionally provides the benefit of increasing the burst strength of the macro-capsule barrier.

PMCG has previously only been used as an integral polymer during formation of the membrane (Wang et al., *Transplantation*, 85(3): 331-7 (2008)). In contrast, the macro-capsule design described herein does not employ PMCG as an integral part of the membrane, but instead as a coating material that binds to and occupies exposed, non-bound sulfate groups of cellulose sulfate.

Thus, in some embodiments, the process of preparing a macro-capsule comprising cellulose sulfate includes a step of washing the macro-capsule with PMCG after polymerization with pDADMAC. When preparing macro-capsules comprising more than one barrier, the process can comprise a sequential PMCG wash step after the polymerization of each subsequent barrier.

After the capsules have been fully prepared, the macro-capsules can be rinsed and returned to cell culture media.

The macro-capsules can be adhered to a piece of surgical mesh by placing the macro-capsule in contact with the surgical mesh. An amount of cellulose sulfate is added to cover the portions of the macro-capsules and the surgical mesh that are in contact. Alternatively, an amount of cellulose sulfate and glucomannan is added to cover the portions of the macro-capsules and surgical mesh that are in contact. Polymerizing solution of pDADMAC is added to bind the macro-capsules and surgical mesh together.

IV. Devices Comprising the Disclosed Macro-Capsules

The macro-capsules described herein can be attached or combined into larger structures (i.e., devices) that are capable of providing more therapeutic cells (e.g., islet cells or insulin-producing cells) to a subject in need thereof. For example, therapeutic cell-based devices comprising a plurality of the disclosed macro-capsules can be prepared by joining multiple macro-capsules end-to-end, or by attaching the macro-capsules to a therapeutically suitable substrate, such as a surgical mesh.

In general, the disclosed devices will comprise two or more macro-capsules. For example, the devices may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 or more of the disclosed macro-capsules.

The devices may comprise a therapeutically suitable substrate to which the macro-capsules are attached. In some embodiments, the substrate may be a surgical mesh, such as a nylon mesh, but the substrate is not particularly limited so long as it is generally unreactive with the subject's immune system.

When surgical mesh or a similar material is used for the substrate, macro-capsules may be attached in a variety of ways. For example, the macro-capsules may be arranged radially around the mesh, in apposition along the mesh, or arranged to extend on opposite sides of the mesh. FIG. 9 provides several exemplary arrangements.

Additionally, when surgical mesh or a similar material is used for the substrate, it may be fabricated into various shapes that may be useful for fitting specific implantation sites. For instance, the surgical mesh or similar substrate may be round or oblong or another shape that those of skill in the art would deem appropriate for implantation.

In some embodiments, the substrate (e.g., the surgical mesh) may comprise a tab that functions as a suture point to allow for easy attachment and detachment of the device to the implantation site within the subject. In some embodiments, the substrate (e.g., the surgical mesh) may be directly sutured or otherwise affixed to the implantation site within the subject.

Implantation sites for the disclosed devices can include, but are not limited to, the greater omentum, an omentum pouch, and/or the peritoneal cavity.

V. Methods of Treatment

As noted above, the macro-capsules described herein can encapsulate therapeutic cells (e.g., islet cells or insulin-producing cells), and therefore the disclosed macro-capsules and devices are useful in methods of treating diabetes in a subject in need thereof. In some embodiments, the subject is a human subject with insulin-dependent diabetes.

The methods generally involve implanting a therapeutically effective amount of insulin-producing cells encapsulated in the macro-capsules disclosed herein into a subject in need thereof. Thus, in some embodiments, the methods comprise implanting into an individual in need thereof a therapeutically effective amount of insulin-producing cells encapsulated in macro-capsules comprising at least two barriers and having diameters of at least 1.5 mm. In some embodiments, the methods comprise implanting into an individual in need thereof a therapeutically effective amount of insulin-producing cells encapsulated in macro-capsules comprising at least one barrier in which the outer barrier is comprised of (i) cellulose sulfate and glucomannan or glucomannan sulfate or (ii) sodium alginate. In some embodiments, the methods comprise implanting into an individual in need thereof a therapeutically effective amount of insulin-producing cells encapsulated in macro-capsules formed in the shape of a cylindrical tube comprised of an inner capsule of alginate and an outer capsule of cellulose sulfate and glucomannan sulfate. In some embodiments, the disclosed methods comprise implanting into a subject in need thereof at least one of the disclosed devices comprising at least two of the macro-capsules described herein.

In some embodiments, the methods comprise implanting into an individual in need thereof a therapeutically effective amount of insulin-producing cells encapsulated in the disclosed macro-capsules or devices about once a year, once every two years, once every three years, once every four years, once every five years, or more. In some embodiments, the implanted cells will survive for at least six months after implantation. Accordingly, in some embodiments, the subject may require only one implant. In some embodiments, the implant may need to be replaced once every 6, 7, 8, 9, 10, 11, 12, 13, 14, 15, 16, 17, or 18 or months, once every 1, 2, 3, 4, or 5 or more years or until the subject has recurring hyperglycemia, or a return to the diabetic state.

In some embodiments, the encapsulated cells or devices are implanted to the greater omentum of the subject. The greater omentum (also known as the great omentum, omentum majus, gastrocolic omentum, epiploon, or, caul) is a large apron-like fold of visceral peritoneum that hangs down from the stomach and extends from the greater curvature of the stomach back to ascend to the transverse colon before reaching to the posterior abdominal wall. Thus, the encapsulated cells or devices may be implanted into a pouch formed surgically from the omentum.

In some embodiments, the encapsulated cells or devices are attached to the omentum of the subject. A device comprising a piece of surgical mesh can be sutured to an edge of the omentum by passing a suture through the mesh and the omentum. Thus, the encapsulated cells may be implanted to the omentum without forming a pouch from the omentum.

In some embodiments, the encapsulated cells or devices are implanted into the peritoneal cavity. In some embodiments, the encapsulated cells or devices are implanted into the peritoneal cavity and anchored to the omentum. In some embodiments, the encapsulated cells or devices are implanted into an omentum pouch. In some embodiments, the macrocapsule is a cylindrical tube, and in some embodiments, the encapsulated cells are implanted into the peritoneal cavity with one end of the cylindrical tubes anchored to the omentum.

Exemplary doses of encapsulated cells can vary according to the size and health of the individual being treated. For example, in some embodiments, an exemplary implant of cells encapsulated in the disclosed macro-capsules may comprise 5 million cells to 10 million cells per Kg of body weight. The disclosed macro-capsules and devices are capable of encapsulating a therapeutically effective amount of cells; for example, at least about 50,000 cells per cm, at least about 60,000 cells per cm, at least about 70,000 cells per cm, at least about 80,000 cells per cm, at least about 90,000 cells per cm, or at least about 1000,000 cells per cm or more.

Furthermore, the disclosed methods of treatment can additionally comprise the administration of a second therapeutic in addition to the encapsulated therapeutic cells. For example, in some embodiments, the additional therapeutic compound can include, but is not limited to, insulin injections, metformin, sulfonylureas, meglitinides, thiazolidinediones, DPP-4 inhibitors, GLP-1 receptor agonists, and SGLT2 inhibitors.

Particular treatment regimens comprising implanting the disclosed macro-capsules may be evaluated according to whether they will improve a given patient's outcome, meaning it will help stabilize or normalize the subject's blood glucose levels or reduce the risk or occurrence of symptoms or co-morbidities associated with diabetes, including but not limited to, episodes of hypoglycemia, elevated levels of glycosylated hemoglobin (HbA1C levels), heart disease, retinopathy, neuropathy, renal disease, hepatic disease, periodontal disease, and non-healing ulcers.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from diabetes, increasing the quality of life of those suffering from diabetes, decreasing the dose of other medications required to treat diabetes, delaying or preventing complications associated with diabetes, and/or prolonging survival of individuals.

Furthermore, while the subject of the methods is generally a subject with diabetes, the age of the patient is not limited. The disclosed methods are useful for treating diabetes across all age groups and cohorts. Thus, in some embodiments, the subject may be a pediatric subject, while in other embodiments, the subject may be an adult subject.

One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure. The following examples are given to illustrate the present invention. It should be understood, however, that the invention is not limited to the specific conditions or details of these examples.

EXAMPLES

Example 1—Formation and Testing of Macro-Encapsulated Cells

Sulfation of Cellulose:

Cellulose was sulfated similarly to the methods used by Zhang et al., *Cellulose*, 17:427-435 (2010). Briefly, cellulose was suspended in anhydrous dimethyl formamide (DMF) and slowly mixed with a solution of DMF/acetic anhydride/chlorosulfonic acid and was stirred at 50° C. for 5 hours. The mixture was then poured into a saturated solution of anhydrous sodium acetate in ethanol. The precipitate was centrifuged and washed with 4% sodium acetate in ethanol. The precipitate was collected and mixed with 1M ethanolic sodium hydroxide for 15 h at room temperature. The pH was adjusted to 8 with a 50/50 mixture of acetic acid/ethanol. The precipitate was washed with ethanol and dissolved in DI water. The solution was filtered through a 0.45 um filter, dialyzed in DI water, and lyophilized.

Sulfation of Glucomannan:

Glucomannan was suspended in a solution of dimethylsulfoxide. Pyridine sulfate was added dropwise to the glucomannan solution and the reaction was raised to 60° C. for 2 hours. The reaction was cooled to room temperature and the pH was adjusted to 8 with a solution of sodium hydroxide. The glucomannan sulfate was precipitated with ethanol and resuspended in water. The solution was dialyzed against distilled water for 48 hours and filtered through a 45 um filter.

Differentiation of Glucose-Sensing, Insulin-Expressing Cells:

A stem cell line (SR1423) cultured in E8 medium (Life Technology) on tissue culture dishes coated with geltrex (Life Technology) was detached from the substrate by exposure to 0.5 mM EDTA and transferred to a suspension culture dish in E8 medium supplemented with 10 nM Rho Kinase inhibitor (Y-27632, Sigma). The culture dish was placed on an orbital shaker rotating at 70-90 RPM in a humidified tissue culture incubator at 37° C. and 6% $CO_2$ overnight. The clusters that were formed were removed from the orbital shaker, collected and re-suspended in DMEM containing 0.2% human serum albumin, 0.5×N2 supplement (Life Technology), 0.5× B27 supplement (Life Technology), 1× penicillin/streptomycin (VWR), Activin A (100 ng/ml) and Wortmannin (1 nM). The culture media was changed daily for three or four days. The clusters were collected and re-suspended in a 50/50 solution of RPMI/F12 containing 0.2% human serum albumin, 0.5× B27 supplement, 0.5× Insulin-transferrin-selenium supplement (VWR), 1× penicillin/streptomycin (VWR), retinoic acid (2 uM), KGF (50 ng/ml), Noggin (50 ng/ml), and Cyclopamine (250 nM). The media was changed daily for 4 days. The clusters were collected and re-suspended in DMEM low glucose supplemented with glucose to 8 mM, 0.5% human serum albumin, 0.5× Insulin-transferin-selenium supplement, 1×N2 supplement, 1× penicillin/streptomycin, KGF (50 ng/ml), Noggin (50 ng/ml), and EGF (50 ng/ml). The media was changed every other day for 4 days. The clusters were collected and re-suspended in DMEM low glucose supplemented with glucose to 8 mM, 0.5% human serum albumin, 0.5× Insulin-transferrin-selenium supplement, 1×N2 supplement, 1× penicillin/streptomycin, Noggin (50 ng/ml), EGF (50 ng/ml), GSiXXI (1 uM), Alk5i (10 uM), and T3 (1 uM). The media was changed every other day for 4 days. The clusters were collected and re-suspended in DMEM low glucose supplemented with glucose to 8 mM, 0.5% human serum albumin, 0.5× Insulin-transferin-selenium supplement, 1×N2 supplement, 1× penicillin/streptomycin, Betacellulin (20 ng/ml), Retinoic Acid (100 nM), Alk5i (10 uM), and T3 (1 uM). The media was changed every other day for 4 days. The clusters were collected and re-suspended in CMRL 1066 supplemented with glucose to 8 mM, 0.5% human serum albumin, 0.5× Insulin-transferin-selenium supplement, 1×N2 supplement, 1× penicillin/streptomycin, 1× Glutamax (Life Technology), Nicotinamide (10 mM]) BMP4 (10 ng/ml), Alk5i (10 uM), and T3 (1 uM).

Cell Encapsulation:

A population of cells comprised of 100,000 or more glucose-sensing, insulin expressing cells was suspended in a volume of 1.8% cellulose sulfate/0.1% glucomannan in 130 mM NaCl, 10 mM 3-(N-morpholino)propanesulfonic acid (MOPS), pH 7.4. to achieve a density of 2 million cells per ml. The cellulose sulfate/glucomannan/cell mixture was transferred to a non-stick surface composed of poly-ethylene and allowed to drip into a stirred solution of 1% Poly (diallyldimethylammonium chloride) (pDADMAC), 130 mM NaCl, 10 mM 3-(N-morpholino)propanesulfonic acid (MOPS), pH 7.4. Upon contact, the cellulose sulfate polymerizes with the pDADMAC to form a membrane around the cells in the form of a spherical macro-capsules that is greater than 2 mm in diameter. The macro-capsule was collected with a wide-bore pipette and transferred to a solution of pDADMAC, 130 mM NaCl, 10 mM MOPS, containing 0.3% Poly(methylene co-guanidine) (pMCG), pH 7.4. The macro-capsules were collected and rinsed two times in 130 mM NaCl, 10 mM MOPS, pH 7.4. The macro-capsules were collected and mixed with a 1% solution of pDADMAC and stirred for 2 minutes. The macro-capsules were collected and rinsed briefly in distilled water. The macro-capsules were then submerged in a solution of 1.8% cellulose sulfate/0.1% glucomannan in 130 mM NaCl, 10 mM MOPS, pH 7.4 for 2 minutes. The macro-capsules were collected and transferred to a solution of 130 mM NaCl, 10 mM MOPS, 0.3% Poly(methylene co-guanidine) (pMCG), pH 7.4. Finally, the macro-capsules were rinsed four times in a solution of 130 mM NaCl, 10 mM MOPS, pH 7.4, transferred to culture medium and incubated in a humidified incubator at 37° C. and 6% $CO_2$.

This process formed a macro-capsule composed of an inner membrane that contains the insulin-expressing cells and an outer membrane that is closely associated with the inner membrane (FIG. 1A). The membrane formed with glucomannan limits the accumulation of host cells to the surface, thereby inhibiting fibrosis (FIG. 1).

Figure 2:
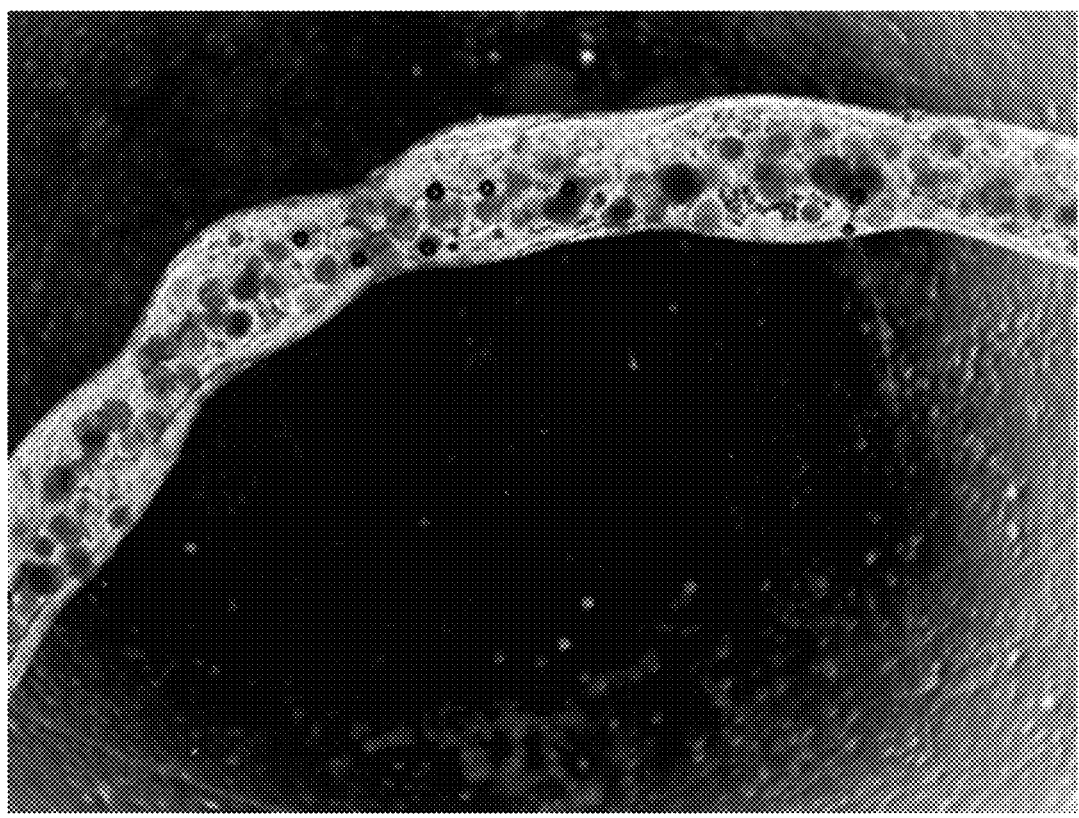
FIG. 2 shows a double layer macro-capsule comprised of an inner capsule formed from sodium alginate and an outer capsule formed from cellulose sulfate and konjac glucomannan sulfate. This macrocapsule has a non-spherical shape.

In another example: A population of cells comprised of 1,000,000 or more glucose-sensing, insulin expressing cells was suspended in a volume of 2% sodium alginate in 130 mM NaCl, 10 mM 3-(N-morpholino)propanesulfonic acid (MOPS), pH 7.4. to achieve a density of 2 million cells per ml. The alginate/cell mixture was transferred to a syringe with an inner bore size of 1 mm and dispensed into a bath of 20 mM $BaCl_{10}$ mM MOPS, 100 mM mannitol, pH 7.4. to create a hydrogel in the form of a cylindrical tube. The tube-shaped macro-capsules were collected with a wide-bore pipette and rinsed two times in 130 mM NaCl, 10 mM MOPS, pH 7.4. The macro-capsules were collected and mixed with a 1% solution of pDADMAC and stirred for 2 minutes. The macro-capsules were collected and rinsed briefly in distilled water. The macro-capsules were then submerged in a solution of 1.8% cellulose sulfate/0.1% glucomannan sulfate in 130 mM NaCl, 10 mM MOPS, pH 7.4 for 2 minutes. Finally, the macro-capsules were rinsed four times in a solution of 130 mM NaCl, 10 mM MOPS, pH 7.4, transferred to culture medium and incubated in a humidified incubator at 37° C. and 6% $CO_2$ (FIGS. 1 and 2).

Capsule Permeability.

Permeability of the macro-capsules was determined by incubation for 1 hour in the presence of FITC-conjugated dextran polymers of defined molecular weight. After 1 hour, the dextran solution was rinsed from the outside of the macro-capsules. FITC-dextran that was able to passively diffuse across the capsule membrane remains within the capsule during the rinse and fluoresces. Double-layered macro-capsules formed from cellulose sulfate without glucomannan were not permeable to 20 kDa Dextran. Double-layered macro-capsules formed from a mixture of cellulose sulfate and glucomannan were permeable to 20 kDa FITC-dextran but not 70 kDa dextran (FIG. 3).

Formation of Device:

A piece of nylon surgical mesh was cut to form a rectangular shape 2 cm long and 1 cm wide with a single tab extending from the side (FIG. 9). Four macro-capsules were aligned in parallel in a petri dish. The mesh was placed to cover the ends of the macro-capsules. A drop of 1.8% cellulose sulfate/0.1% glucomannan sulfate in 130 mM NaCl, 10 mM MOPS, pH 7.4 cellulose sulfate solution was added to cover the portions of the macro-capsules and the surgical mesh that were in contact. Polymerizing solution of 1% pDADMAC, 130 mM NaCl, 10 mM MOPS, was added to bind the macro-capsules and surgical mesh together. The polymerization was allowed to proceed for 2 minutes before rinsing 4× in 130 mM NaCl, 10 mM MOPS, and returning to cell culture media.

Rat Model of Insulin-Dependent Diabetes:

Immune competent Sprague-Dawley rats of at least 8 weeks of age and at least 200 g body weight were fasted for 2-6 hours and administered 60-65 mg/kg streptozotocin via I. V. into the tail vein. Animals were considered diabetic if they demonstrated 3 consecutive days of non-fasting glucose levels >300 mg/dl. Glucose levels were stabilized after confirmed hyperglycemia by subcutaneous implant of an insulin slow-release pellet (Linplant; Linshin, Scarborough, Canada). Glucose was monitored by collecting a drop of blood via tail prick or the lateral saphenous vein, and applied to a portable glucose meter.

Engraftment of Capsules/Cells to Rats.

A ventral midline skin incision was made in the upper abdomen. The abdominal wall was tented and sharply incised at the midline of rectus abdominis. The abdomen was accessed and the omentum was isolated and externalized. The spherical macro-capsules were placed between two thin sheets of gelfoam and placed in the center of the omentum. The corners of the isolated portion of omentum were folded over the graft to create a pouch, which was then closed with sutures. The omental pouch was positioned back in the abdominal cavity and the abdominal incision was sutured followed by the skin using surgical staples.

Engraftment of Non-Spherical, Tube-Shaped Capsules to Peritoneum of Rats.

An abdominal incision was made through the dermis and the abdominal wall. The tube-shaped macro-capsule was introduced to a wide-bore pipette. The pipette was introduced into the peritoneal cavity and the macro-capsule slowly ejected. The abdominal wall and dermis were closed with sutures.

Engraftment of Non-Spherical, Tube-Shaped Capsules Anchored to the Omentum of Rats.

An abdominal incision was made through the dermis and the abdominal wall. A portion of the omentum was externalized. The piece of surgical mesh attached to the macro-capsule was laid upon the omentum. A suture joined the mesh to the omentum. The tube-shaped macro-capsule and externalized portion of the omentum were introduced back into the peritoneum. The abdominal wall and dermis were closed with sutures.

Figure 4:
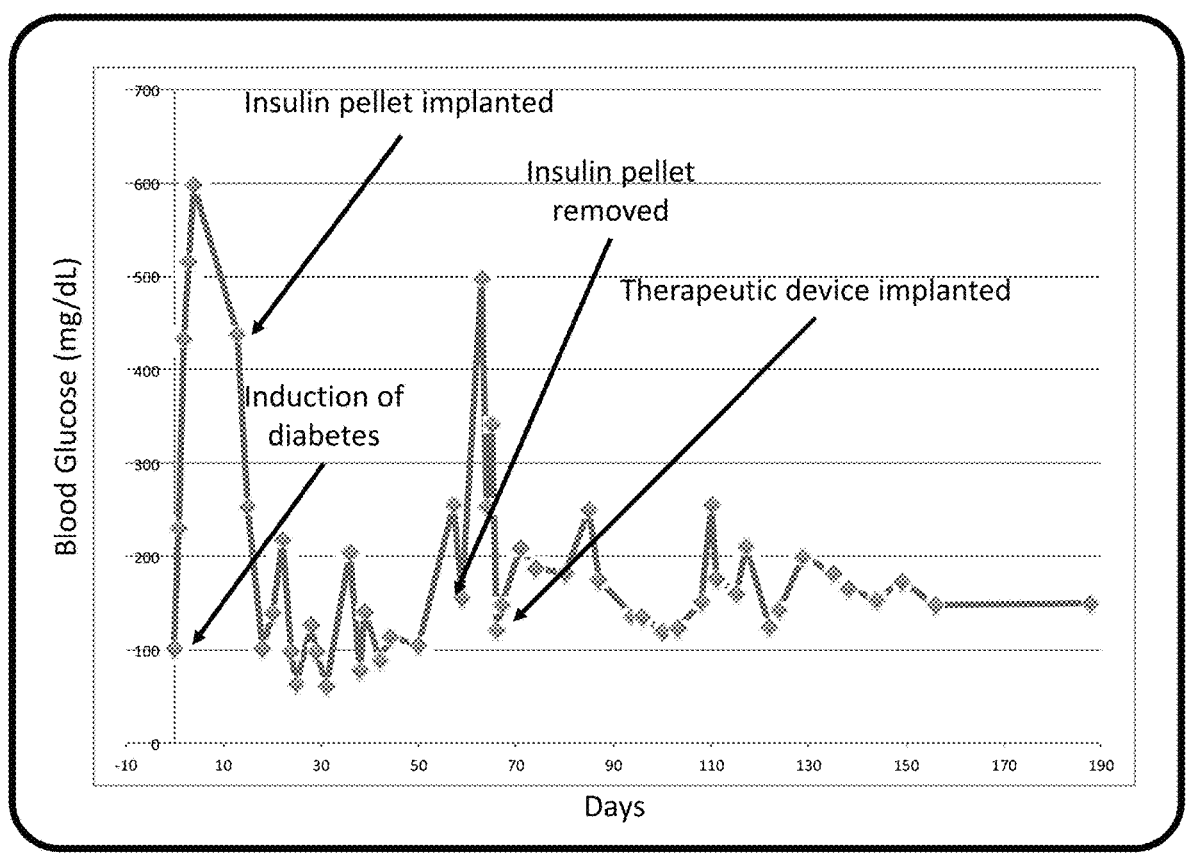
FIG. 4 shows regulation of blood glucose in diabetic rats. Normal Sprague-Dawley rats were rendered diabetic by injection of streptozotocin on day 0, leading to a rapid elevation of blood glucose concentration. To keep the animal healthy, a slow release insulin pellet was implanted under the skin on day 13. On day 67, the insulin pellet was removed and macro-capsules containing insulin-producing cells were surgically engrafted to the omentum. Blood glucose concentration remained controlled.

Regulation of Blood Glucose:

Immune competent rats that had been rendered diabetic by treatment with streptozotocin regained normoglycemia after omental implant of macro-capsules containing insulin-expressing cells (FIG. 4).

Figure 5A:
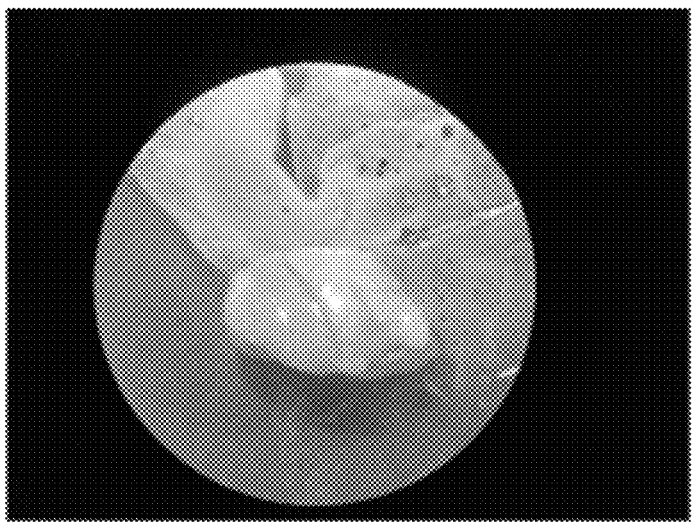
FIGS. 5A-5C show explants of macro-capsules from rodents. Three weeks post-implant into diabetic rats, the omental pouch containing macro-capsules was removed. (A) shows the pouch was well-vascularized. (B) and (C) depict immunofluorescence analysis showing that the macro-capsules within the explant contain insulin-expressing cells. (B) and (C) show the surface of the macro-capsules are free from host cell attachment or evidence of inflammation and fibrosis.
Figure 5B:
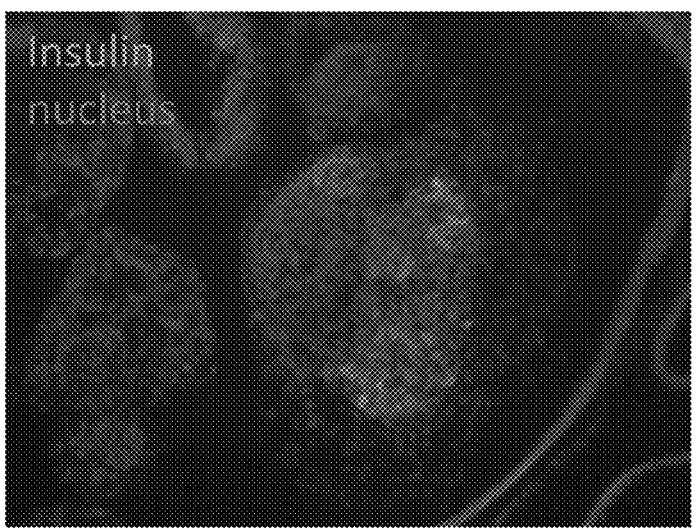
Figure 5C:
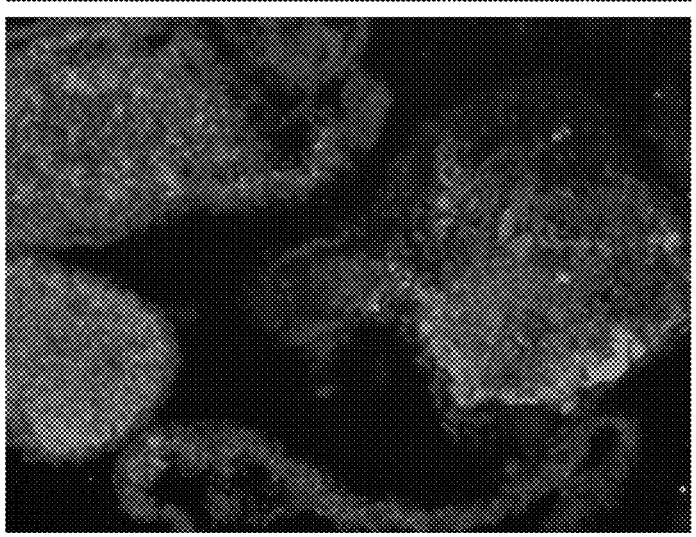
Figure 6A:
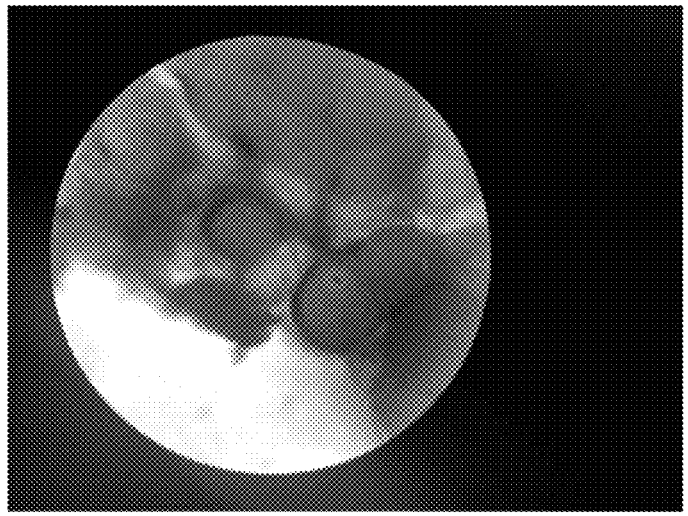
FIGS. 6A-6C show explants of macro-capsules from rodents. (A) spherical macro-capsules within a pouch formed from the omentum were explanted three weeks post-implant into diabetic rats. The macro-capsules are visible as spheres within a transparent omental membrane. The membrane shows a dense network of microvessels in close proximity to the macro-capsules. (B, C) Cylindrical macro-capsules were explanted three weeks post-implant into diabetic mice. The macro-capsules were adhered to the omentum of the host. Vasculature from the omentum is evident in close proximity to the macro-capsules.
Figure 6B:
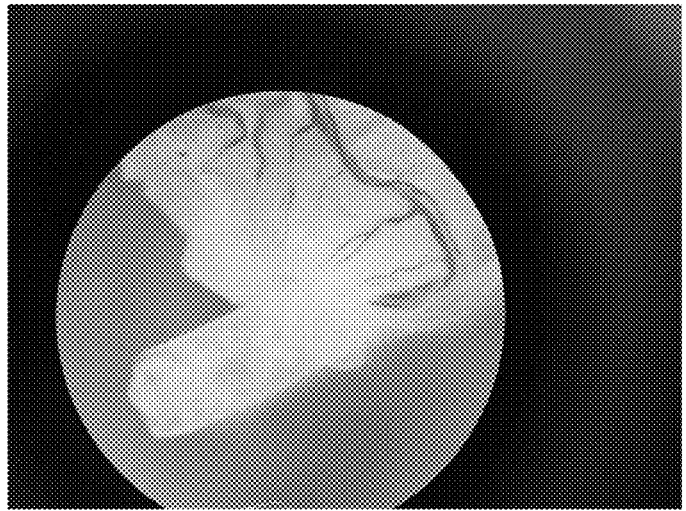
Figure 6C:
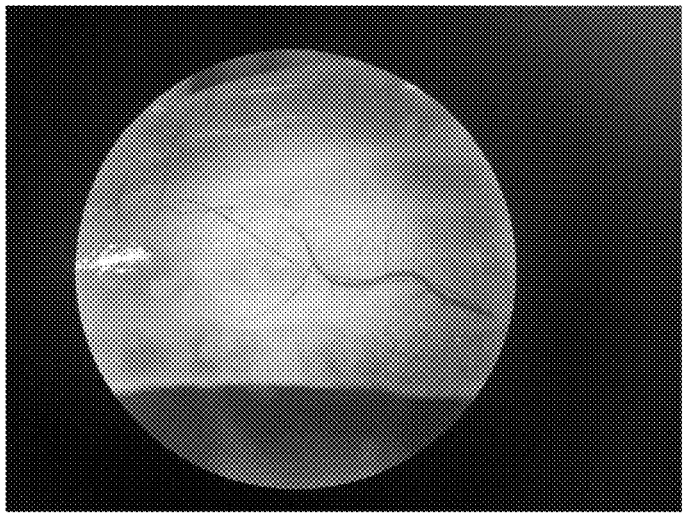
Figure 7A:
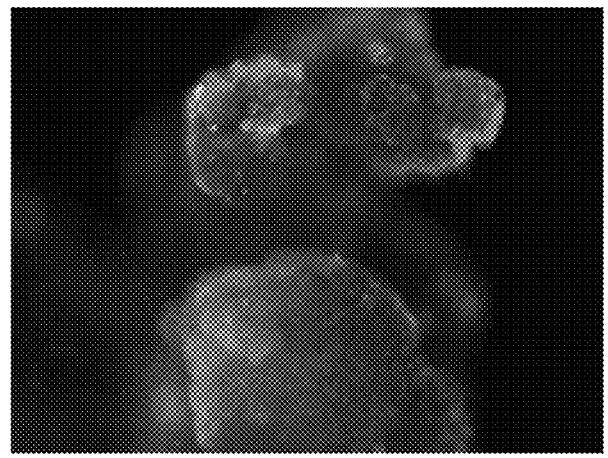
FIGS. 7A-7C show that the macro-capsules enable the survival of implanted xenogeneic cells. Clusters of therapeutic human cells were evaluated for cell viability by staining with fluorescent indicators of living (green) and dead (red) cell. Clusters of cells are equally viable before implant (A) as after 9 days (B) and 47 days (C) after implant to a normal immune-competent mouse.
Figure 7B:
Figure 7C:
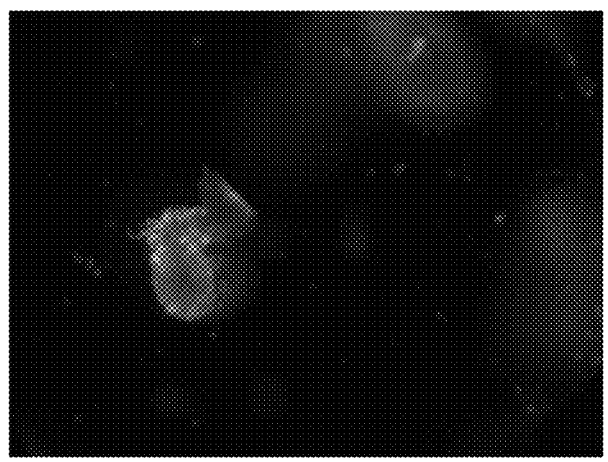
Figure 8A:
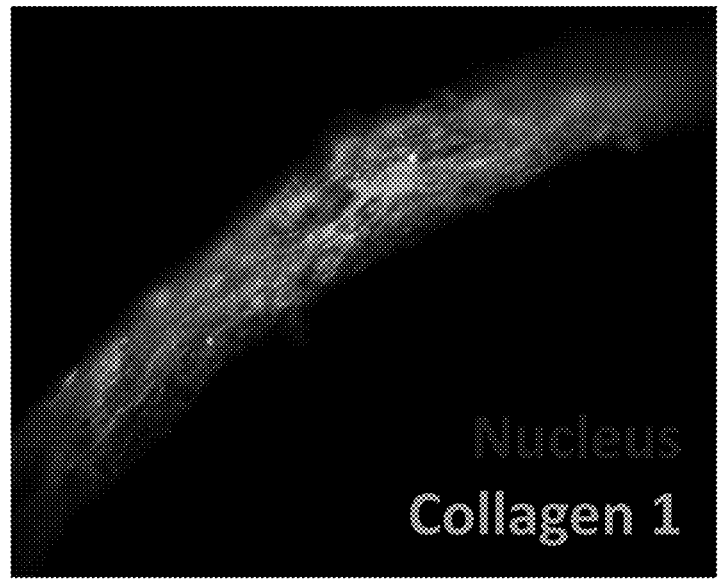
FIGS. 8A-8B show the membrane, originating from the omentum, around the explanted macro-capsule six months after implant. (A) The membrane is thin, cellularized, and contains collagen. Original magnification is 400×. (B) The macro-capsule contains insulin-expressing cells six months after implant.
Figure 8B:
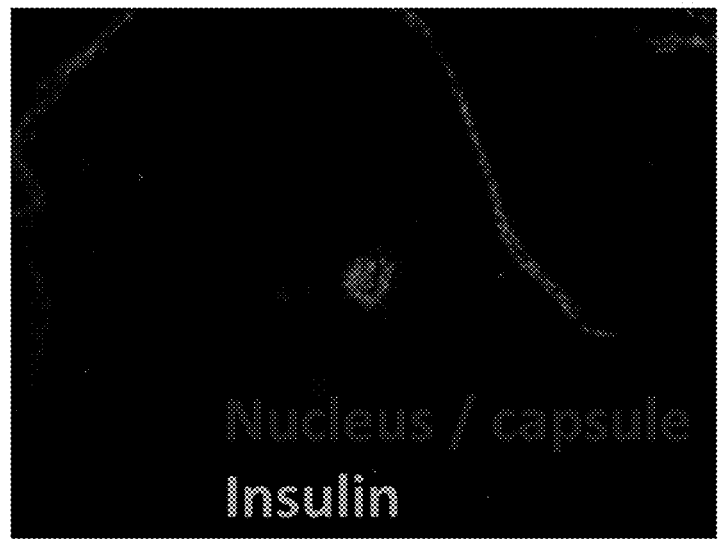
Figure 9A:
FIGS. 9A-9F show the structures of devices formed with cylindrical macro-capsules. (A) Single macro-capsule (x) attached to surgical mesh (y) useful as anchor point to host tissue. (B) A plurality of macro-capsules are attached to a strip of surgical mesh in apposition. The mesh is formed to have one or more tabs (z) useful for attaching the device to a tissue of the host such as the omentum. A device with two (2) tabs is shown. (C) Macro-capsules (x) are attached to a strip of surgical mesh (y) on opposite sides of the mesh. The mesh is formed to have one or more tabs (z) useful for attaching the device to a tissue of the host such as the omentum. A device with two (2) tabs is shown. (D) Macro-capsules (x) are attached to a circular piece of surgical mesh (y) radially outward from the center. The mesh is formed to have one or two tabs (z) useful for attaching the device to a tissue of the host such as the omentum. A device with two (2) tabs is shown. (E) Macro-capsules (x) are attached to a strip of surgical mesh (y), and the mesh can be formed into a tab (z) useful for attaching the device to a tissue of the host. (F) Macro-capsules (x) are attached to a strip of surgical mesh (y) in a spiral pattern, and the mesh can be formed into a tab (z) useful for attaching the device to a tissue of the host.
Figure 9B:
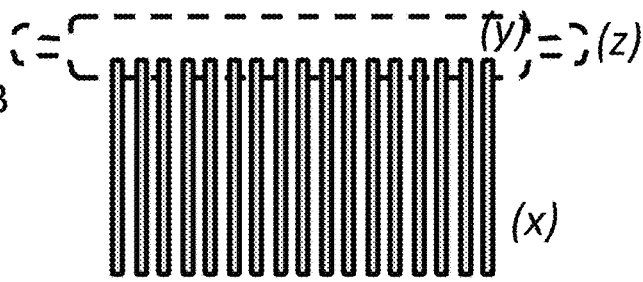
Figure 9C:
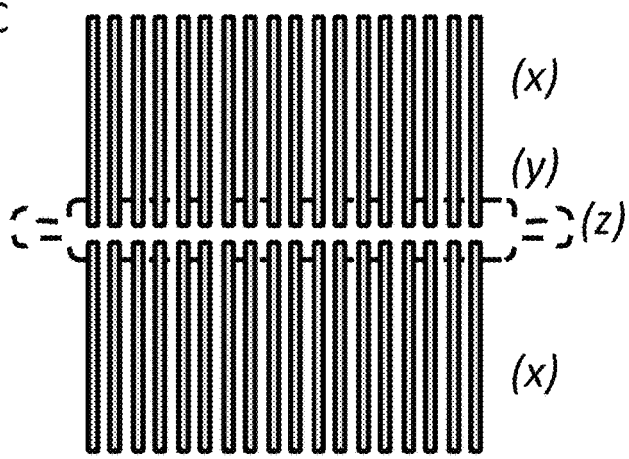
Figure 9D:
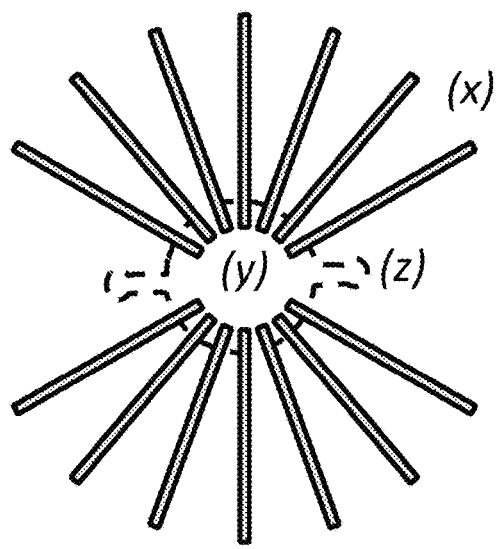
Figure 9E:
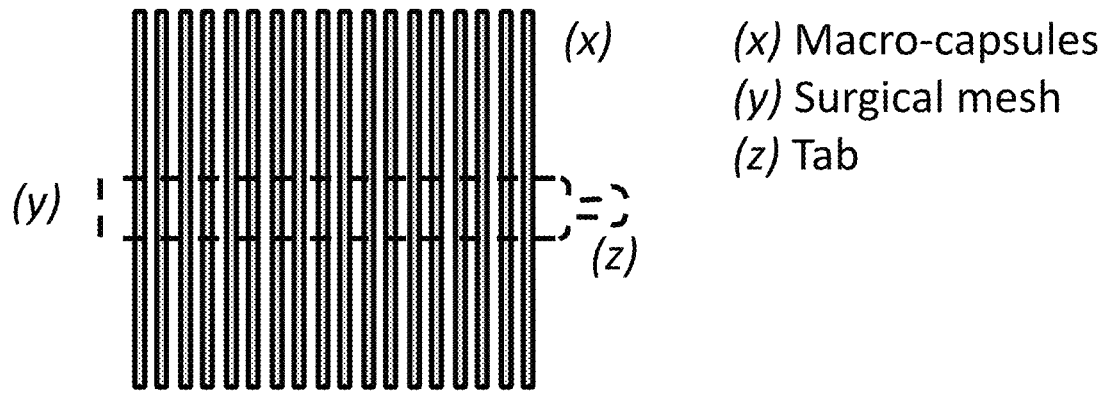
Figure 9F:
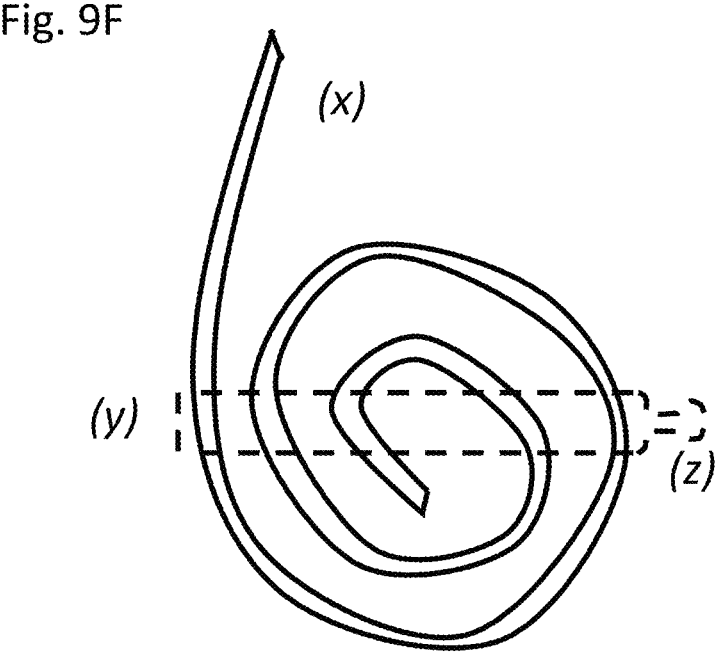

Explant of Macro-Capsules:

Rats were euthanized by sedation with ketamine followed by intracardiac injection of potassium chloride. The omental pouch containing the macro-capsules was excised. Alternatively, the attachment of the cylindrical macro-capsule device to the omentum was cut by scissors and the device was removed. The morphology of the explants and evidence of vascularization was photographed (FIG. 6). The explants were rinsed in PBS and stained for viable and dead cells using the Live/Dead cell staining kit (Biovision) and following manufacturers instructions (FIG. 7). The explanted devices were preserved in 4% formalin. The devices were embedded in optimal cutting temperature compound (OCT), frozen and sectioned to 10 um thickness with a cryotome. The sections were applied to microscope slides and stained for expression of insulin and collagen 1 using standard immunohistochemistry techniques. Macro-capsules exhibited only a thin membrane adhere to the surface of the macro-capsules (FIG. 8A). The macro-capsules contained clusters of viable, insulin-expressing cells (FIG. 8B; see also FIG. 5).

Example 2—Treating Diabetes with the Disclosed Encapsulated Cells

This example illustrates methods of using macro-encapsulated cells as described herein to treat Type I diabetes in a human adult.

An adult human subject with insulin-dependent diabetes receives a transplant comprising a therapeutically effective amount of a composition comprising the disclosed macro-encapsulated islet cells into the subject's omentum pouch, anchored to the omentum, or into the peritoneal cavity. The subject is evaluated for blood glucose levels. The subject is monitored following the implant of a therapeutically effective number of macro-encapsulated cells to ensure that the subject's blood glucose levels have been stabilized. The subject is further screened for glycosylated hemoglobin, and co-morbidities of diabetes over time.

What is claimed is:

1. A device comprising a piece of surgical mesh and a plurality of macro-capsules encompassing a plurality of therapeutic cells, the macro-capsule comprising a first barrier and a second barrier encompassing the first barrier, wherein the first barrier comprises:
   (a) cellulose sulfate and glucomannan or glucomannan sulfate; or
   (b) sodium alginate,
   wherein the macro-capsule has a cylindrical shape and a diameter of at least 1.5 mm, and
   wherein the macro-capsules are attached to the piece of surgical mesh.

2. The device of claim 1, wherein the surgical mesh is nylon.

3. The device of claim 1, wherein the surgical mesh is round.

4. The device of claim 1, wherein the surgical mesh is oblong.

5. The device of claim 1, wherein the surgical mesh comprises a tab for attaching the device to a suitable site within the host.

6. The device of claim 1, wherein the macro-capsules are arranged radially around the mesh.

7. The device of claim 1, wherein the macro-capsules are arranged in apposition along the mesh.

8. The device of claim 1, wherein the macro-capsules are arranged to extend on opposite sides of the mesh.

9. A method of treating diabetes in a subject in need thereof, comprising implanting into a subject with diabetes the device of claim 1, wherein the device is implanted into the greater omentum or the peritoneal cavity of the subject.

10. A composition comprising a cylindrical macro-capsule encompassing a plurality of insulin-producing therapeutic cells, the macro-capsule comprising a first barrier and a second barrier, the first barrier comprising:
    (a) cellulose sulfate and glucomannan or glucomannan sulfate; or
    (b) sodium alginate;
    wherein the macro-capsule is attached to a piece of surgical mesh to which at least one other macro-capsule is also attached, and wherein the diameter of the macro-capsule is at least 1.5 mm.

11. The composition of claim 10, wherein the second barrier comprises cellulose sulfate and glucomannan or glucomannan sulfate.

12. The composition of claim 10, wherein the second barrier does not comprise glucomannan or glucomannan sulfate.

13. The composition of claim 10, wherein the diameter of the macro-capsule is at least 2.0 mm.

14. The composition of claim 10, wherein the sodium alginate is polymerized with divalent cations barium ($BaCl_2$) or calcium ($CaCl_2$)).

15. The composition of claim 10, wherein the cellulose sulfate was polymerized with poly(diallyldimethylammonium chloride) (pDADMAC).

16. The composition of claim 10, wherein the macro-capsule was washed with polymethylene-co-guanidine (PMCG) after polymerization with pDADMAC.

17. The composition of claim 10, wherein the macro-capsule is at least about 11 cm in length.

18. The composition of claim 10, wherein the macro-capsule contains at least about 50,000 cells per cm.

19. A composition comprising a plurality of macro-capsules encompassing a plurality of insulin-producing therapeutic cells, each macro-capsule comprising at least a first barrier and a second barrier, wherein the first barrier is encompassed within the second barrier, wherein each macro-capsule has a diameter of at least 1.5 mm, and wherein each macro-capsule in the plurality of macro-capsules is attached to a piece of surgical mesh.

20. The composition of claim 19, wherein the diameter of the macro-capsule is at least 2.0 mm.

21. The composition of claim 19, wherein the second barrier comprises cellulose sulfate and glucomannan or glucomannan sulfate.

22. The composition of claim 19, wherein both the first and second barrier comprise cellulose sulfate and glucomannan sulfate.

23. The composition of claim 21, wherein the cellulose sulfate was polymerized with pDADMAC.

24. The composition of claim 22, wherein the cellulose sulfate was polymerized with pDADMAC.

25. The composition of claim 23, wherein each macro-capsule was washed with PMCG after polymerization with pDADMAC.

26. The composition of claim 24, wherein each macro-capsule was washed with PMCG after polymerization with pDADMAC.

27. The composition of claim 19, wherein the second barrier does not comprise glucomannan or glucomannan sulfate.

28. The composition of claim 19, wherein the first barrier comprises sodium alginate.

29. The composition of claim 28, wherein the sodium alginate is polymerized with divalent cations barium ($BaCl_2$) or calcium ($CaCl_2$)).

30. The composition of claim 19, wherein each macro-capsule is at least about 11 cm in length.

31. The composition of claim 19, wherein each macro-capsule contains at least about 50,000 cells per cm.

32. The composition of claim 19, wherein each macro-capsule is cylindrical.

33. A composition comprising a macro-capsule encompassing at least 50,000 insulin-producing therapeutic cells per cm, the macro-capsule comprising a cylindrical shape, a length of at least 11 cm, and a diameter of at least 1.5 mm, wherein the macro-capsule is attached to a piece of surgical mesh to which at least one other macro-capsule is also attached, wherein the macro-capsule comprises at least a first barrier and a second barrier, wherein the first barrier is encompassed within the second barrier, and wherein the first barrier comprises: (a) cellulose sulfate and glucomannan or glucomannan sulfate; or (b) sodium alginate.

34. The composition of claim 33, wherein the second barrier comprises cellulose sulfate and glucomannan or glucomannan sulfate.

* * * * *